United States Patent [19]

Razzano

[11] Patent Number: 5,510,441
[45] Date of Patent: * Apr. 23, 1996

[54] PROCESS FOR PRODUCING OCTAMETHYLTRISILOXANE

[75] Inventor: John S. Razzano, Cohoes, N.Y.

[73] Assignee: General Electric Company, Waterford, N.Y.

[*] Notice: The portion of the term of this patent subsequent to May 30, 2012, has been disclaimed.

[21] Appl. No.: 294,808

[22] Filed: Aug. 25, 1994

Related U.S. Application Data

[63] Continuation-in-part of Ser. No. 92,450, Jul. 15, 1993, Pat. No. 5,420,221.

[51] Int. Cl.⁶ .................................................. C08G 77/08
[52] U.S. Cl. .................................. 528/12; 528/20; 528/21; 528/23; 528/33
[58] Field of Search ................................. 528/21, 23, 33, 528/20, 12

[56] References Cited

U.S. PATENT DOCUMENTS

| | | |
|---|---|---|
| 3,706,775 | 12/1972 | Nitzsche et al. . |
| 4,203,903 | 5/1980 | Evans .............................. 549/361 |
| 4,902,813 | 2/1990 | Wegehaupt et al. . |
| 5,210,131 | 5/1993 | Gilson et al. ........................ 524/14 |

*Primary Examiner*—Melvyn I. Marquis

[57] ABSTRACT

The present invention is concerned with the use of linear phosphonitrilic chloride catalyst to make low molecular weight linear siloxanes.

9 Claims, 3 Drawing Sheets

PROCESS FOR PRODUCING OCTAMETHYLTRISILOXANE

This application is a continuation-in-part of Applicant's co-pending application Ser. No. 08/092,450 filed Jul. 15, 1993, U.S. Pat. No. 5,420,221, which is incorporated by reference.

The present invention relates to a novel process of making low molecular weight linear siloxanes. More particularly, it is concerned with the use of linear phosphonitrilic chloride catalyst to rearrange M and D species to make low molecular weight siloxanes such as octamethyltrisiloxane and decamethyltetrasiloxane.

BACKGROUND OF THE INVENTION

Octamethyltrisiloxane, also referred as MDM, can be effectively used as a solvent in electronic device cleaning systems. It is known in the art to use a Filtrol based equilibration process to equilibrate MM and a D source to give as high as possible level of MDM followed by Filtrol filtration and product distillation. The MDM content at equilibrium is low, with large quantities of MM and $MD_xM$, $x>1$. The MM and higher boilers can be recycled. Although eventually the overall conversion of M and D to MDM is high with recycle, the process pound per pound of product is also very high. Further, the use of Filtrol and the necessity of filtration on each pass make the overall process efficiency even lower. The manufacture flow is so complicated and time-consuming that the manufacturing cost becomes too high.

In a application Ser. No. 08/092,450 filed Jul. 15, 1993, U.S. Pat. No. 5,420,221, Applicant and his co-inventors described a novel process which is characterized as a disproportionation reaction. Applicants discovered that if two or more M and D containing polymers, which have different molecular weights, are combined at weight ratios of from about 1:99 to 99:1 or more preferably from 5:95 to 95:5 in the presence of a condensation/disproportionation catalyst, such as a linear phosphonitrilic chloride, an extremely fast and complete siloxane disproportionation reaction takes place between M and D containing polymers. The reaction results in the formation of a lower molecular weight product than one of the two starting materials without the formation of substantial amount of cyclics.

Applicant continued his research to develop a new and simple method for large production of low molecule weight siloxanes such as octamethyltrisiloxane and decamethyltetrasiloxane.

SUMMARY OF THE INVENTION

According to the present invention, a novel method is provided for making octamethyltrisiloxane and other low molecular weight linear siloxanes. The process comprises the steps of using linear phosphonitrilic chloride (hereinafter "LPNC") to equilibrate siloxane mixture comprising trimethylsiloxanes and dimethylsiloxanes, preferably consisting essentially of hexamethyldisiloxanes (hereinafter "MM units") and diorganosiloxanes (hereinafter "D units"). The LPNC catalyst provides for very fast siloxane rearrangement in the absence of silanol or excessive amount of water. The reaction does not require the filtration step.

DETAILED DESCRIPTION OF THE INVENTION

Figure 1:
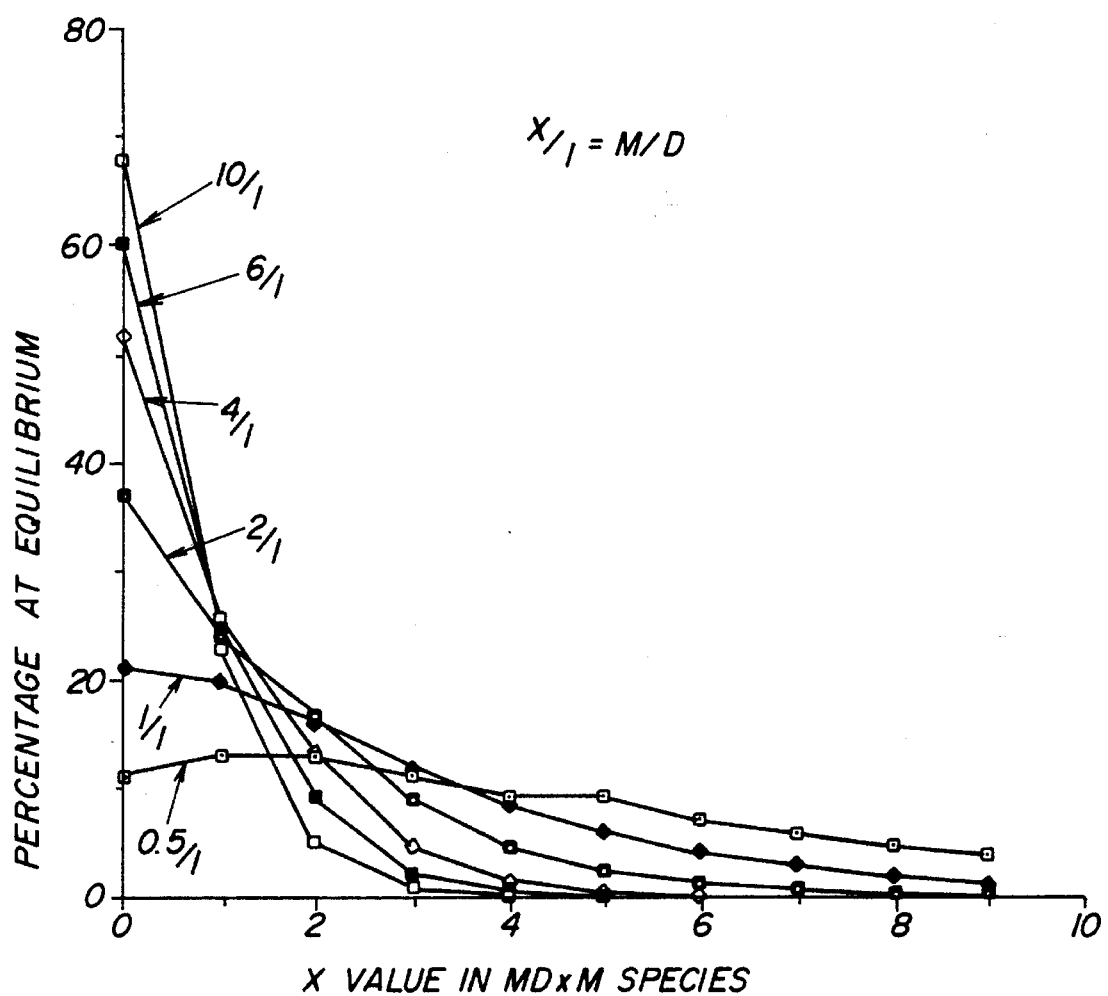
FIGS. 1, 2 and 3 compare the percent at equilibrium with the M/D ratio or the X value in the $MD_xM$ species.

The present provides an efficient method to produce low molecular weight linear siloxanes have the general formula $$MD_xM$$

wherein M is trimethylsilane, D is dimethylsiloxane, x is an integer greater than 0.

The starting materials employed in the present invention is a siloxane mixture containing MM units and D units. The MM and D units can be any of the existing silicone products, from silicone fluids to gums. The preferred ratio between MM and D units is 0.5:1 to 10:1.

Among the most preferred catalysts for use in the practice of the invention are included phosphorus-nitrogen compounds which have been utilized in the prior art as condensation catalysts for making high molecular disilanols. Some of these catalysts are described in U.S. Pat. Nos. 5,210,131; 4,203,903; and 3,706,775, all of which are incorporated by reference. Illustrative, but not limitative of such useful phosphorus-nitrogen catalysts include $Cl_3PN(PNCL_2)_xPCl_3 \cdot PCl_6(x=1)$(LPNC) and short-chain linear phosphazenes of Formulae (Ia) or (Ib):

$$O(X)_{2-m}Y_mP\{NP(X)_2\}_nNP(X)_{3-q}(Y)_q \qquad (Ia)$$

$$O(X)_{2-m}Y_mP\{NP(X)_2\}_nNHP(O)(X)_{2-p}(Y)_p \qquad (Ib)$$

where n=0 or an integer from 1 to 8; m=0 or an integer of 1; p=0 or an integer of 1; q=0 or an integer of from 1 to 2; X=halogen; Y=OH, OR, O(O)CR, wherein R is alkyl or aryl, as catalysts for polycondensation and redistribution of organopolysiloxanes.

Also contemplated are reaction products of the linear PNC compounds with compounds containing active protons with pKa values below 18, such as carboxylic acids, halogenoalkane carboxylic acids, sulfonic acids, alcohols, phenols. Cyclic PNC compounds, such as $(PNCL_2)_x$ also operate but are very slow compared to linear catalysts. $Cl_3PN(PNCL_2)_xPCl_3 \cdot PCl_6(x=1)$ is the most preferred catalyst.

The amount of the catalyst that is employed is an effective amount to readily disproportionate the siloxane system. The amount to be employed is not critical and may vary from 5 to 500 parts per million and more preferably from 10 to 100 parts per million of total weight of the organosiloxane starting materials used in the practice of the invention. Higher amount of catalyst will be used with high silanol content in the starting materials, e.g., 1000 to 3000 ppm of silanol. First, an effective amount of PNC catalyst is added to the reactor to condense the starting material until the Si—OH content is reduced to below about 1000 ppm. A second increment of the PNC catalyst is then added to effect the disproportionation reaction.

The catalyst is preferably dispersed or dissolved in an inert medium at a concentration of from 0.1 to 10 weight percent and preferably 0.5 to 5 weight percent in order to facilitate the handling of the catalyst and to facilitate dispersing the catalyst in the reaction mixture. Suitable solvents for the catalyst include esters, such as aliphatic ethers, aromatics, such as toluene, benzene, liquid siloxanes, chlorinated aliphatic and aromatic organic solvents such as methylene chloride, trichloroethane, 1,3,5-trichlorobenzene and the like.

In the practice of the process of the present invention, it is important that the silanol content of the blended organosiloxanes be low. The general upper limit for silanol content is about 3,000, more preferably 1,000, and most preferably 700 ppm based on the total weight of the organosiloxanes in the blend. At higher silanol contents, the silanol or water of condensation hydrolyzes the LPNC catalyst. The hydrolyzed catalyst is a poor rearrangement catalyst. The problem can be accommodated by first adding a certain amount of LPNC and using the condensation action of LPNC to reduce the silanol below 700 ppm, and then adding fresh LPNC to complete the rearrangement.

After the rearrangement reaction has proceeded to the point where the desired equilibrium has been formed, the reaction is terminated. Since the boiling points for MM, MDM and $MD_2M$ are respectively 100° C., 154° C. and 195° C., it is relatively easy to separate the desired product from the reaction mixture by distillation. When the reaction mixture is subjected to fractional distillation, a large quantity of MM in the reaction mixture will be distilled out prior to the distillation of the product. Thus, the catalyst must be deactivated at the end of the rearrangement and before distillation. If the catalyst is not completely deactivated before distillation of MM, the removal of MM in the presence of the active catalyst will shift the equilibrium concentration of the pot as the reactor MM content is decreased. The catalyst can be chemically deactivated by any of several bases. For example, the catalyst can be inactivated by neutralization with an alkaline material. Suitable alkaline materials include ammonia; hexamethyldisilazane, aliphatic primary., secondary and tertiary organic amines such as ethyl amine, diethyl amine, triethyl amine, propyl amine and the like. The catalyst can also be chemically deactivated by inorganic materials such as sodium hydroxide, calcium oxide and magnesium oxide. The amount of the neutralizing agent which is used should be sufficient to terminate the further rearrangement of M and D in the reaction mixture and provide a stable product. The amount is determined by reference to the total acid content and is generally from 10 to 100 ppm of neutralizing agent based on the total weight of the reactants. If the catalyst is over neutralized with base, excessive amount of LPNC will be needed to re catalyze the successive recycle batches. In the alternative, the catalyst can also be thermally neutralized by raising the temperature to from 130° to 250° C. The temperature is decided by the M/D ratio in the reactor. The higher the MM level is, the lower the pot temperature is. When the M/D ratio is too high, the reactor temperature is likely to be too low to thermally deactivate the batch in a reasonable time. The temperature of the reactor can be raised to a suitable deactivation temperature if the reaction system is allowed to pressurize.

The MM distilled out can be recycled to the reactor at the end of the MDM cut and other low molecular weight linear species such as $MD_2M$, $MD_3M$ to be reequilibrated with the higher boiling species which remain in the reactor prior to the next distillation, along with fresh LPNC, M and D species added to the reactor to preserve the original M/D ratio and the catalyst level.

If the starting materials contain some impurities, such as high level T units, after several recycles, these impurities can buildup in the pot and reduce the efficiencies of the process. The higher the T level is, the fewer the recycles are. At some point, when the T level in the system is too high, the residue recycled stream has to be cleaned up separately.

The rearrangement process can be either a batch process or a continuous process. In a batch process, it is important to choose the optimum M/D ratio to assure (1) an adequate pot temperature for catalyst deactivation in a short time period; (2) a relatively low MM to MDM ratio at equilibrium; and (3) maximum amount of MDM in the reactor prior to distillation. It is possible that at the highest level of MDM, the level of MM to be distilled as a "forecut" is also very high. Therefore, in a batch process, there is an optimum of MM and MDM which produces the highest output of MDM, $MD_2M$, and etc. per process hour, and that this optimum may not be at the maximum level of MDM content.

In a continuous process, the M/D can be less of a consideration since it is possible to design for any level of MM at equilibrium and the optimum process will probably be at the maximum MDM content. The fact that the equilibrium concentration of MM and especially MDM are fairly constant over a wide M/D ratio allows the distillation column portion of the process to operate at steady state even if the concentration in the reactor varies. The ratio of input M to D can be chosen to maximize the MDM, $MD_2M$, etc. in the equilibrate, e.g., at M/D ratios of 2/1 to 6/1. Under such conditions, the ratio of MM to MDM at equilibrium would be high (approximately 1.5/1 to 3.0/1), but this can be easily accommodated in the design of the column. All non product streams would be recycled to a starting reactor. The starting reactor equilibrates the M and D sources in the mixture and the mixture is pumped through a static mixer at high temperature to deactivate the catalyst quickly prior to separation of MM and product fractions in a continuous distillation column designed specifically to isolate products of interest.

A continuous process for higher volume production may require two columns. An equilibrated and deactivated mixture is fed to the first column where either 1) MM is removed at the top, 90% MDM in the middle and heavies at the bottom, or 2) MM and MDM (perhaps 50% MDM) are removed together at the top and heavies at the bottom. The second column does the final purification. It is more efficient to allow the first column to be a part of the continuous system, and the final purification to be done batchwise.

The process can be run in a single reboiler/column type reactor for many recycles by recycling the MM from the first cut of distillation directly to the reboiler with some makeup M and D corresponding to product removed. This has tremendous cost advantages over the prior art processes. The silicones produced by this simple, low cost, fast, low byproduct process has many uses, such as a potential solvent to replace halogenated solvents in the electronics industry,.

DESCRIPTION OF THE PREFERRED EMBODIMENTS

The following examples are included to illustrate the invention. All viscosities were measured at 25° C. Unless otherwise indicated, all parts are by mole.

EXAMPLE 1

The equilibrium compositions of MDxM species, x>0, at various M to D ratios were determined. Appropriate amount of MM and Silicones fluid which viscosity is 350 cps were weighed into vials to produce 20 grams of mixture for each M/D ratio. LPNC catalyst was available as a 2% solution in dimethylsilicone oil (SF-96(20)). 100 ppm of LPNC catalyst (0.1 grams of the catalyst solution) was added to each vial. This level of catalyst was much higher than necessary. The rearrangement takes place with 20–25 ppm LPNC. The excess amount was used to be sure that the experiments would run smoothly. Since the catalyst solution was mostly D silicone, the 0.1 grams of the catalyst solution was counted as part of the D component in preparing the M/D ratios to avoid composition errors at high M/D ratios.

The vials were placed in a boiling water bath for three hours and then cooled to room temperature. 10 microliters of HMDZ were added to in the vials to react with all of the chloride in the LPNC. The solutions turned hazy after a few minutes.

All samples were analyzed on a Hewlett-Packard 5890 GC with a 30 meter capillary column and a thermal conductivity detector. The GC analysis produced an area percent for each component. Retention factors for each component were not determined and only area percents were reported.

TABLE 1*

|  | A | B | c | D | E | F |
|---|---|---|---|---|---|---|
| M/D RATIO | 0.5/1 | 1/1 | 2/1 | 4/1 | 6/1 | 10/1 |
| MM | 11 | 21 | 37 | 51.6 | 60 | 68 |
| MDM | 13 | 20 | 24 | 25.8 | 25 | 23 |
| MD2M | 12.6 | 16.4 | 16.7 | 13.6 | 9.2 | 5 |
| MD3M | 11.4 | 12.1 | 9.0 | 4.8 | 2.3 | 0.9 |
| MD4M | 9.4 | 8.6 | 4.7 | 1.6 | 0.6 | 0.2 |
| MD5M | 9.4 | 6.0 | 2.5 | 0.5 | 0.2 | — |
| MD6M | 7.1 | 4.2 | 1.3 | 0.17 | — | — |
| MD7M | 5.8 | 2.9 | 0.7 | 0.1 | — | — |
| MD8M | 4.8 | 1.9 | 0.4 | — | — | — |
| MD9M | 3.8 | 1.3 | 0.23 | — | — | — |
| D4 | 3.0 | 1.3 | 0.4 | 0.15 | 0.12 | — |

*Small peaks (<0.1%) are not reported.

The data indicates that as the M/D ratio was increased, there was a regular shift to lower molecular linears and a greater quantity of MM at equilibrium. It has now surprisingly been found that the % MDM only changed by a small amount (20–26%) over the M/D range of 1:1 to 10:1. This relative insensitivity of MDM content over these ranges is particularly advantageous for control of a continuous process. Also, the percent of $MD_2M$ content changed by only a small amount (13.6–16.7%) over the range of 1:1 to 4:1.

Figure 2:
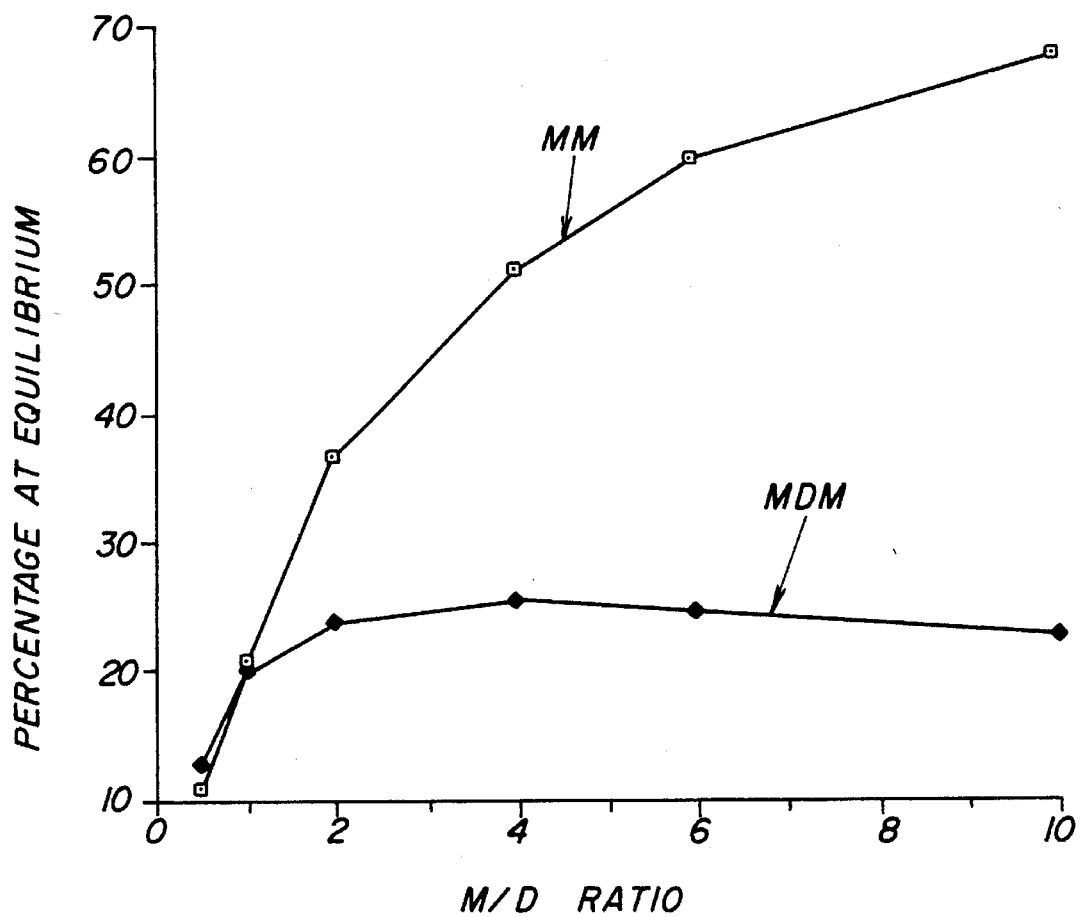

FIG. 2 is a plot of the MM and MDM percentage of each equilibrate as a function of M/D. It is constructed to show the percentage of the batch produced as MM and MDM, and the ratio MM to MDM as function of M/D ratio.

TABLE 2

| M/D Ratio | % MM | % MDM | % (MM + MDM) | MM/MDM |
|---|---|---|---|---|
| 0.5/1 | 11 | 13 | 24 | 0.85 |
| 1/1 | 21 | 20 | 41 | 1.05 |
| 2/1 | 37 | 24 | 61 | 1.54 |
| 4/1 | 51.5 | 25.8 | 77.3 | 2.0 |
| 6/1 | 60 | 25 | 85 | 2.4 |
| 10/1 | 68 | 23 | 91 | 2.95 |

The results clearly show the relative insensitivity of the MDM and $MD_2M$ contents as a function of M/D ratio. This is because one pound of D produces 3.18 pounds of MDM, providing major leverage in converting what seems to be a huge excess of M into MDM at high M/D ratios. The MM content at equilibrium only doubled as the M/D ration increases from 2/1 to 10/1.

Figure 3:
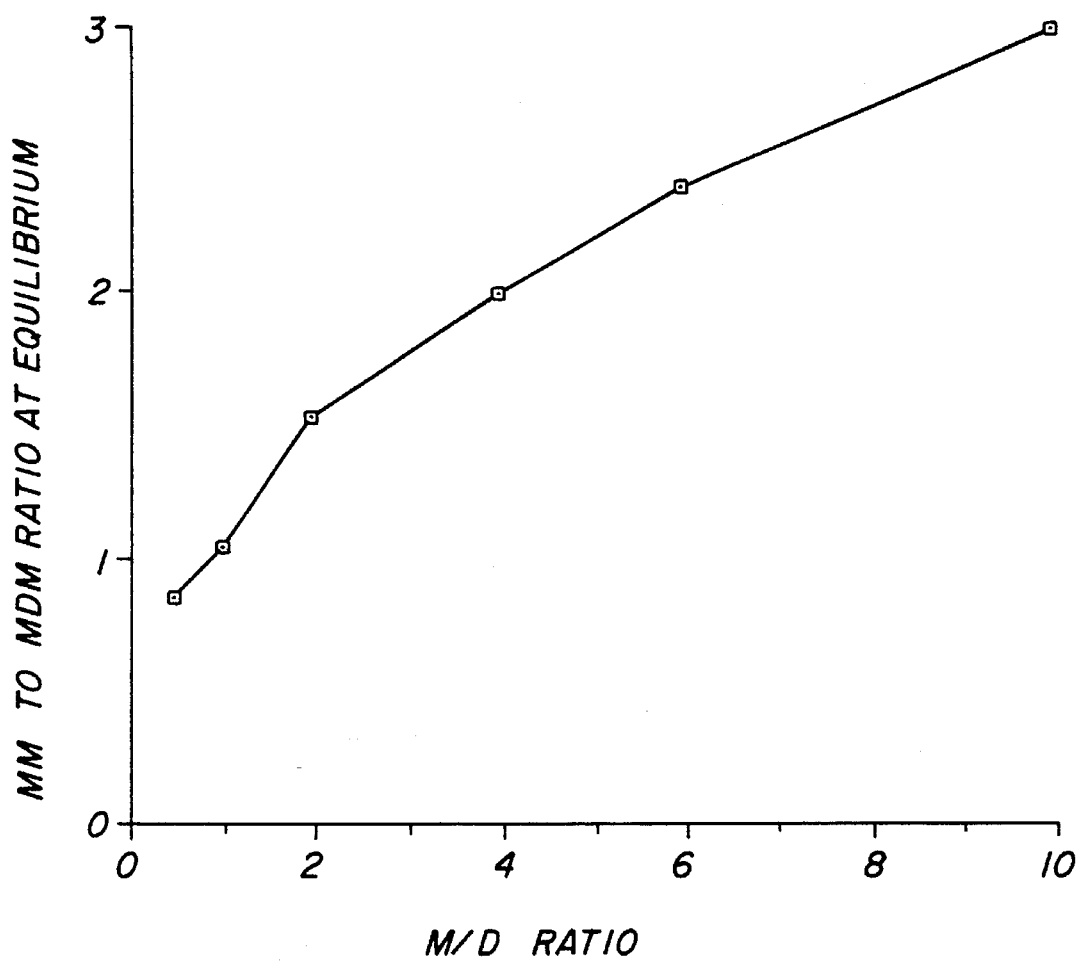

FIG. 3 is a plot, however, of the ratio of MM to MDM as a function of M/D showing the increasing inefficiencies of distillation as the M/D ration increases.

An M/D ratio of 1/1 requires the distillation of only one pound of MM per pound of MDM, but these two species comprise only 41% of the pot contents at this M/D, requiring substantially more reactor batches per pound of output.

EXAMPLE 2

As an approach to determining the optimum conditions for a batch process, MM and the silicone fluid at a 1/1 M/D molar ratio were added to a flask and the system was brought to reflux. The pot temperature at reflux was 104° C. 100 ppm of LPNC was added. The temperature steadily rose to 149° C. over a two hour period. The batch was held at reflux for 2 more hours to ensure thermal catalyst deactivation. At this point, additional MM was added to the flask so that the M/D ratio was 2/1. The pot temperature stabilized at 130° C. An additional 100 ppm LPNC was added to the flask. The pot temperature rose to 138° C. This indicates that the original reaction of 2 hours at 149° C was adequate to completely deactivate the catalyst. The result also shows that the rearrangement starts easily after the recycle MM and more LPNC are added to the batch.

As shown in Table 2, for a 10M pound batch, only about 4M of the batch need to be distilled to produce about 2M pounds of MDM, and if desired, to produce 1.6M of $MD_2M$. At an M/D ratio of 4/1, 7.7M pounds would have to be distilled to produce 2.4M of product. Since the batch recycle/turnarounds appear easy with LPNC, and since the thermal deactivation time would be long at the equilibrium pot temperature at a 2/1 or greater M/D ratio, the high M/D ratios are not favored. When the M/D ratio is greater than 2/1, the equilibrium pot temperature can be raised to a suitable deactivation temperature if the reaction system is allowed to pressurize.

Although specific examples of the invention have been described herein, it is not intended to limit the invention solely thereto but to include all variations and modifications falling within the spirit and scope of the appended claims.

What is claimed is:

1. A process for producing low molecular weight linear siloxanes of the formula:

$$MD_xM$$

wherein M is trimethylsiloxane, D is dimethylsiloxane, x is an integer greater than 0, said process comprising the steps of (A) mixing silicones comprising hexamethyldisiloxane units with silicones comprising diorganosiloxane units;

(B) adding a catalytic amount of a rearrangement catalyst into the mixture of said step (A) causing siloxane rearrangement;

(C) deactivating the rearrangement catalyst; and (D) collecting the low molecular weight linear siloxanes.

2. The process of claim 1, wherein the molar ratio between the hexamethyldisiloxane units and the diorganosiloxane units is 0.5:1 to 10:1.

3. The process of claim 2, wherein the mixture of said step (A) has a silanol content of less than 3000 ppm.

4. The process of claim 3, wherein the silanol content of the mixture of said step (A) is less than 1000 ppm.

5. The process of claim 4, wherein the silanol content of the mixture of said step (A) is less than 700 ppm.

6. The process of claim 1, wherein the rearrangement catalyst is selected from the group consisting essentially of phosphonitrilic chloride, oxygenated phosphonitrilic chloride, carboxylic acids, halogenoalkane carboxylic acids, sulfonic acids, alcohols, phenols and phosphonitrile halide.

7. The process of claim 6, wherein said phosphonitrile halide catalyst has the general formula $[X(PX_2=N)_nPX_3]+ [MX_{(v-t)}R^2_t]^-$ where X denotes a halide atom, M is an element having an electronegativity on Pauling's scale of from 1.0 to 2.0, $R^2$ is an alkyl group having up to 12 carbon atoms, n is an integer with a value of from 1 to 8, v is the valence or oxidation state of M and $0<t<v$.

8. The process of claim 1, wherein the low molecular weight siloxane is an octamethyltrisiloxane.

9. The process of claim 1, wherein the low molecular weight siloxane is decamethyltetrasiloxane.

* * * * *